United States Patent
Salys

[11] Patent Number: 5,980,528
[45] Date of Patent: Nov. 9, 1999

[54] HAND OPERABLE PNEUMATICALLY DRIVER CONTROLLABLE PULSE MEDICAL ACTUATOR

[76] Inventor: Scott Casimer Salys, 9006 Scotsman Dr., Austin, Tex. 78750

[21] Appl. No.: 08/848,801
[22] Filed: May 1, 1997
[51] Int. Cl.⁶ ................................................. A61B 17/92
[52] U.S. Cl. ............................. 606/99; 606/100; 606/86
[58] Field of Search ................................. 605/86, 99, 100

[56] References Cited

U.S. PATENT DOCUMENTS

| | | |
|---|---|---|
| 3,922,902 | 12/1975 | Jarman . |
| 4,072,042 | 2/1978 | Servin et al. . |
| 4,073,181 | 2/1978 | Steinmann, Jr. . |
| 4,122,699 | 10/1978 | Logsdon . |
| 4,187,708 | 2/1980 | Champoux . |
| 4,495,791 | 1/1985 | Kemnitz et al. . |
| 5,352,230 | 10/1994 | Hood ............................................ 606/99 |

Primary Examiner—Michael Buiz
Assistant Examiner—David O. Reip
Attorney, Agent, or Firm—Casimer K. Salys

[57] ABSTRACT

Hand operable pneumatically driven medical actuator and method of use preferably utilized for orthopedic or orthodontic manipulation in a user enabled pulse modulated mode. In one form, the medical actuator includes a free piston moveable within the body of the actuator responsive to pressurized gas selectively injected through a valve controlled by the hand supporting the actuator. The valve is operable in both pulse width and pulse frequency modulation modes, initiating corresponding pneumatic forces and acceleration effects on the free piston. A piston stop attached to a shaft extending from the medical actuator converts piston momentum into pulses of force transferable through the shaft to a translation device external to the medical actuator. The force pulses conveyer to the orthopedic or orthodontic translation device act upon teeth, bones, implants, or the like. Pulse modulation in a single hand operating mode permits the user to impart precise dynamic forces to the thing being manipulated.

20 Claims, 3 Drawing Sheets

HAND OPERABLE PNEUMATICALLY DRIVER CONTROLLABLE PULSE MEDICAL ACTUATOR

FIELD OF THE INVENTION

The present invention relates in general to orthopedic and orthodontic medical equipment. More particularly, the invention is directed to a hand operated pneumatically driven actuator suitable to produce selectively characterized pulses of force in a medical environment.

BACKGROUND OF THE INVENTION

The translation of bones or implants attached thereto during surgery, whether it be to humans or other animals, often requires the surgeon to carefully apply relatively significant forces. A common solution to accurately controlling the effects of the forces is to apply the forces in pulse increments, with the pulse characteristics defining a pulse force with limited translation. This form of applied force limits the obvious risk of producing an undesired excess in the translation of a bone or implant.

The particular context within which the present invention is preferably practiced involves the removal of orthopedic implants. In that context, the surgeon is attempting to forcefully extract implants from bone structure while in a sterile hospital environment with minimum size and power equipment. An existing device for accomplishing this function is often referred to as a "slap hammer", the title due largely to the nature of its operation. The structure and operation are analogous to those utilized by automobile mechanics and body repairmen in moving parts using a sliding hammer tool.

In the context of orthopedic implant extraction, the device consists of a guide rod and a sliding weight. A clamp is affixed to the surgically exposed implant and the device is threaded into the clamp. The sliding weight on the device is thrown upward, generating a jerking force when the momentum of the moving weight is converted to a pulse of force upon striking stop on the end of the guide rod. With repeated throws of the sliding weight the pulses of force extract the implant.

Though the "slap hammer" orthopedic implant extraction device is functional in accomplishing basic removals of implants and the like, it is heavy (5–10 pounds), is awkward to handle (requires two handed operation), and is not readily amenable to changes in force characteristics (intensity and duration) as may be sought during an extraction sequence. Though pneumatically operated hammers are known for automotive applications, their size and control characteristics do not lend themselves to orthopedic implant extraction or the like medical procedures.

Similar controllability concerns exits in the orthodontic practices, where extractions of teeth often occur only when the dentist or oral surgeon is pulling at his or her physical limits.

What is needed is a pneumatically operated medical actuator that has structural features which allow it to be light in weight yet fully capable of significant force pulses, that has actuation characteristics which lend themselves to single hand operation, and that provides control resources suitable to create selective pulses encompassing pulse width as well as pulse frequency modulation. Attainment of the foregoing beneficial features should not be done at the sacrifice of structural simplicity, an important consideration for the cleaning and sterilization associated with medical procedures. Likewise as to the importance of design features which allow use with the gases at the pressures available in conventional medical and dental operating rooms.

SUMMARY OF THE INVENTION

The present invention solves the problems characterizing the "slap hammer" device while providing the attributes pursued for a hand operable pneumatically driven controllable pulse medical actuator through a design comprising, a tubular body having a first and a second end, a free piston slidable within the tubular body, a cap means for closing the first end of the tubular body, a shaft extending through the cap means and the free piston, means attached to the shaft for limiting movement of the piston toward the second end of the tubular body, means for positioning the piston proximate the first end of the tubular body, user controllable means for generating a selective pressure in a region between the piston and the cap means, and means for transferring movement in the shaft to an outside body, the movement of the shaft being responsive to contact between the piston and the means for limiting movement.

In another form the invention is directed to a medical actuator suitable to impart modulated pulses of force through an orthodontic or orthopedic translation device to teeth or bone structure, comprising means for moving a free piston within the medical actuator responsive to an introduction of pressurized gas, means for a user of the medical actuator to selectively modulate the pressurized gas introduced into the medical actuator, means for attaching a shaft extending from the medical actuator to the orthopedic or orthodontic translation device, and means for generating pulsed movement in the shaft responsive to contact between the moving free piston and a piston stop means connected to the shaft.

The invention also encompasses the practice of a method for applying selectively modulated pulses of force using a hand operable medical actuator to which the present invention pertains.

In a particularized practice of the invention, a free piston moveable within the body of a medical actuator is accelerated by pressurized gas. The gas is supplied through a valve modulated by one or more fingers of the hand supporting the actuator. A shaft or rod extends from the medical actuator for connection to the orthopedic or orthodontic translation device to be acted upon. The shaft is connected at one end to pull on such device while the other end has a stop actionable by the free piston. Modulation of the pneumatic valve by the user creates force pulses upon the shaft when momentum in the free piston is translated into pulses of force through contact with the stop on the shaft. The characteristics of the pulses are selected by the user through the regulation of the magnitude and duration of the gas pulses used to accelerate the free piston. With the free piston and shaft movements being independent of the actuator body, the pulses of force on the shaft are effectively isolated from the user hand supporting the medical actuator. The medical device body only experiences the forces associated with accelerating the free piston.

The invention is most notably applicable to the extraction of bone implants. In that context, the forces needed to remove the implant are sufficiently significant that the medical "slap hammer" evolved as a tool of the trade. The present invention replaces the cumbersome two handed tool with a pneumatically actuated function equivalent having controllability heretofore unattainable.

DESCRIPTION OF THE PREFERRED EMBODIMENT

Figure 1:
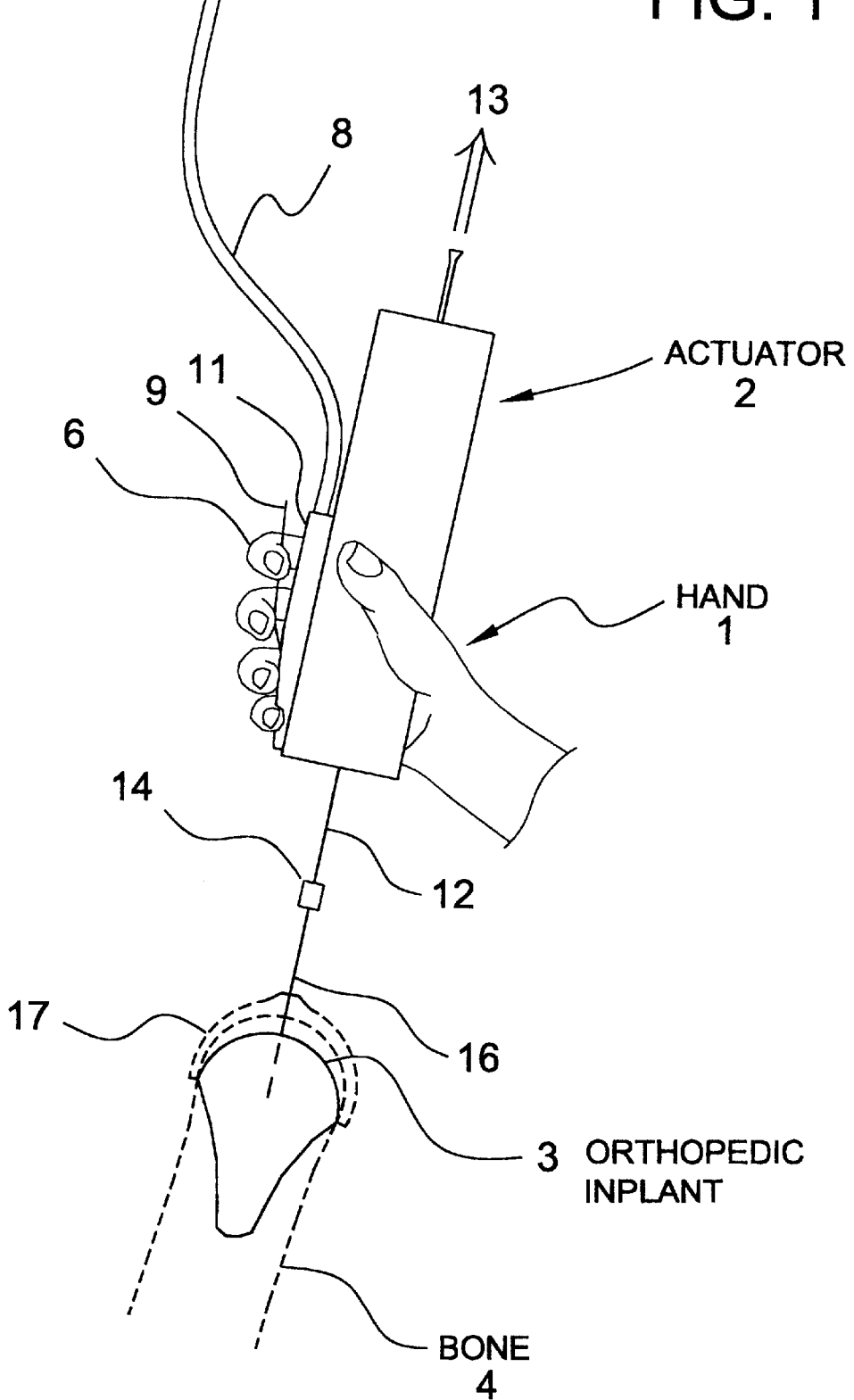
FIG. 1 schematically depicts the use of a medical actuator to impart force pulses to an orthopedic implant.

The invention and use described with reference to the accompanying figures generates user controlled pulses of force in orthopedic and orthodontic applications through a medical actuator operable by a single hand. A representative practice of the invention as applied to the extraction of an orthopedic implant is schematically illustrated in FIG. 1. As depicted in FIG. 1, hand 1 of a human user supports medical actuator 2 while pulses of force are transferred to orthopedic implant 3 in the process of removing implant 3 from bone 4. Index finger 6 of hand 1 selectively modulates the flow of pressurized nitrogen gas 7 furnished through line 8 by actuating lever 9 of gas valve 11. The pulses of force appear along shaft or rod 12 of actuator 2 so as to move shaft 12 predominately in direction 13.

The forces and movements of shaft 12 in direction 13 are generated within actuator 2 when a free piston accelerated in direction 13 by pressurized gas contacts a stop attached to shaft 12. The momentum of the free piston is converted into pulses se force and translation of shaft 12 in direction 13. As shown in FIG. 1, shaft 12 is attached by connection 14 to orthopedic translation device 16, where device 16 is embodied as a shatt threaded into implant 3. Translation device 16 could equally. well be a clamping apparatus, such as shown at 17, if such were the preferred means of imparting the pulling force onto implant 3.

The characteristics of the force pulses and movements of shaft 12 and attached orthopedic translation device 16 are under the direct control of the user in modulating lever 9 of pneumatic valve 9 by index finger 11. The pressurized gas allowed into the body of actuator 2 through valve 11 may be pulse width or pulse frequency modulated to generated force pulses consistent with the needs of the medical procedure. Additionally, the magnitude of the pressure of gas 7 may be adjusted to limit the maximum forces possible as a safety precaution. In this way, the forces can be varied from small, quick tapping pulses to low frequency hammering type forces, including a steady state maximized pulXinJ force, through the selective actuation of gas valve lever 9 by user finger 11.

The operation described above is in contrast to the present practice of using medical "slap hammers" of differing weights depending on the magnitude of the force pulse sought and the strength of the physician, particularly given that orthopedic extractions commonly require that the weight be slid upward. Whereas the strength of the user, the size of the weight and distance of the translation define the characteristics of the forces generated by conventional "slap hammers", such variables are not key to the use of the present invention. Additionally. "medical slap hammers" of traditional design require multi-handed operation, a requirement not particularly popular in a surgical environment.

In relative contrast, consider the present invention as used in FIG. 1. Shaft 12 is independently moveable within the body of actuator 2 as an aspect of imparting force pulses and movements to orthopedic translational device 16. Similarly, the free piston within the body of actuator 2 moves freely between the lower end, as pictured in FIG. 1, of the body and the stop attached to shaft 12. Therefore, the primary forces conveyed to hand 1 in the course of enabling actuator 2 are those attributable to the acceleration of the free piston by entering pressurized gas. Such imputed forces are relatively moderate in peak magnitude given the offsetting inertia of the actuator body elements and user's hand during each pressure initited acceleration cycle of the free piston. The transfer of momentum from the free piston to shaft 12 is relatively isolated from the body of actuator 2.

Figure 2:
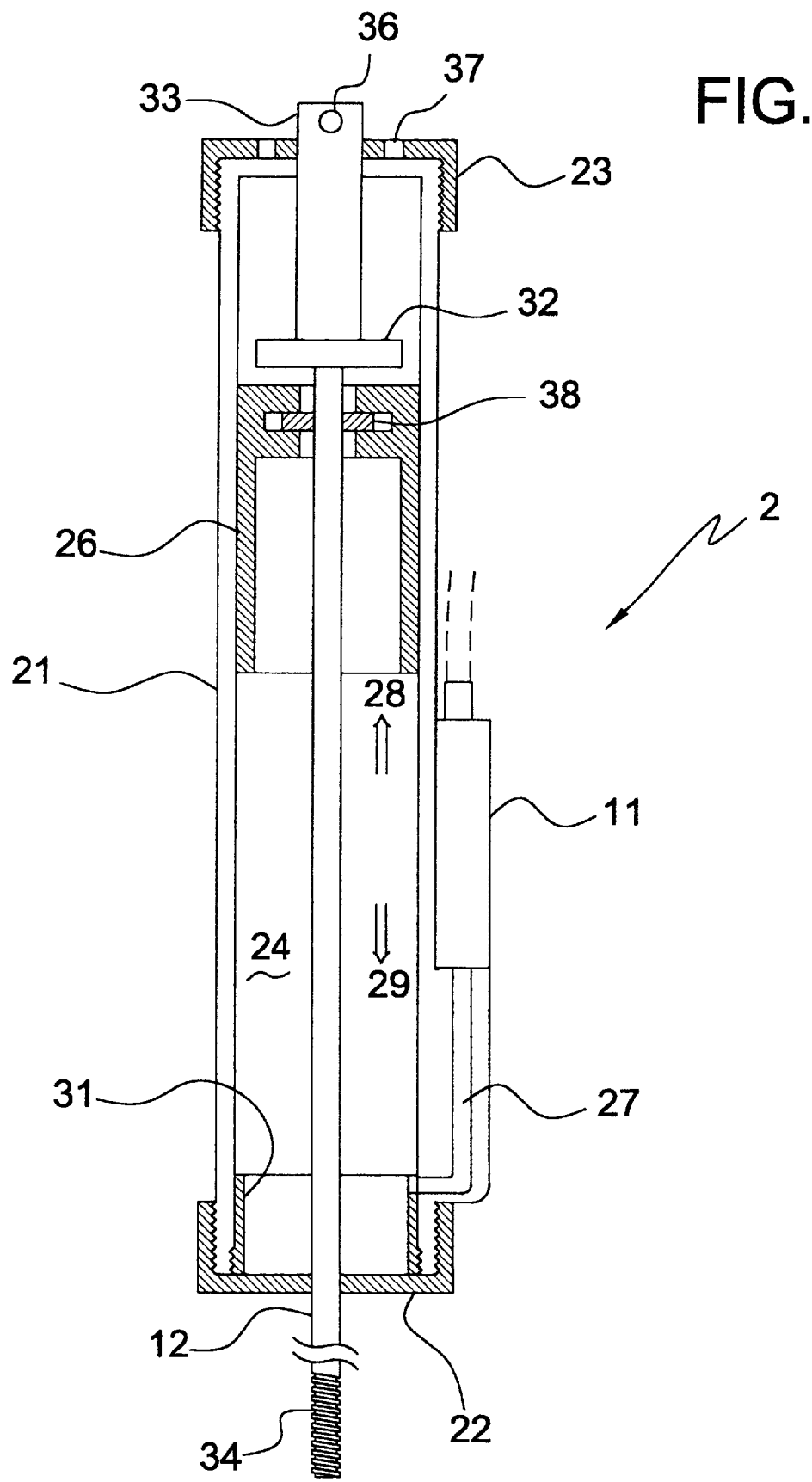
FIG. 2 is a cross-sectional schematic of a medical actuator.

FIG. 2 schematically depicts by cross section a example of actuator 2. The elements are preferably composed of metal or other high temperature material amenable to thorough cleansing and high temperature sterilization. Actuator body 21 is preferably cylindrical with threaded caps 22 and 23 at opposite ends thereof. Both caps 22 and 23 serve to center shaft 12 within body 21, with cap 22 also creating a relatively sealed cavity, generally at 24, between cap 22 and free piston 26.

User hand actuated valve 11 provides pressurized gas through passage 27 into cavity 24 to drive free piston 26 in direction 28. Gravity on the other hand pulls free piston 26 in direction 29 in the typical application where medical actuator 2 is physically oriented in the substantially vertical alignment depicted in FIG. 2. At the vertically lower end of its travel piston 26 comes to rest on travel limiter 31, an element of selectible length depending on the range of travel and Corresponding acceleration desired for piston 26. Namely, the lonner the range of travel the piston is allowed, the greater the momentum and associated peak force pulse upon contact with stop 32 attached to shaft 12.

Though shaft 12 of actuator 2 is preferably round, it can be other cross sections. In the embodiment of FIG. 2, extension 33 of shaft 12 beyond stop 32 is rectangular. The cross sectional asymmetry ensures that shaft 12 does not rotate while transferring pulses of force, for example as might cause treaded end 34 of shaft 12 screwed into translation device 16 (FIG. 1) to unscrew. Pin 36 in extension 33 of shaft 12 limits the downward movement of shaft 12 upon contact with cap 23.

Extension 33 of shaft 12 is freely moveable through cap 23 in that gas sealing is not contemplated for the embodiment in FIG. 2. Actually, holes 37 are provided in cap 23 to allow free upward translation and acceleration of piston 26. In contrast, relative gas sealing is desired between shaft 12 and cap 22, between shaft 12 and piston 26, and between piston 26 and actuator body 21. Though such seals should be reasonably good, they are not critical in that downward translation 29 of piston 26 after a pressurization cycle of cavity 24 can only occur if the pressure bleeds down. Design refinements are likely to include a small controlled bleed port for such cyclic relief of pressure from cavity 24.

Experience has shown that the dimensional tolerances and movements of piston 26 and shaft 12 within body 21 are likely to result in a binding between such elements sufficient to degrade performance. For that reason, piston 26 incorporates floating seal 38, which seal moves within a recess of piston 26 to accomodate axial misalignments while controlling gas leakage around shaft 12. Additionally, both sealing and movement can be improved through the application of coatings, such as Teflon, when applied to the outer walls of free piston 26 and/or the inner walls of actuator body 21. Teflon coating of shaft 12 and floating seal 38 will also improve the delicacy with which pulses of force can be generated on a consistent basis responsive to fine modulation of the gas flow by the user.

Figure 3:
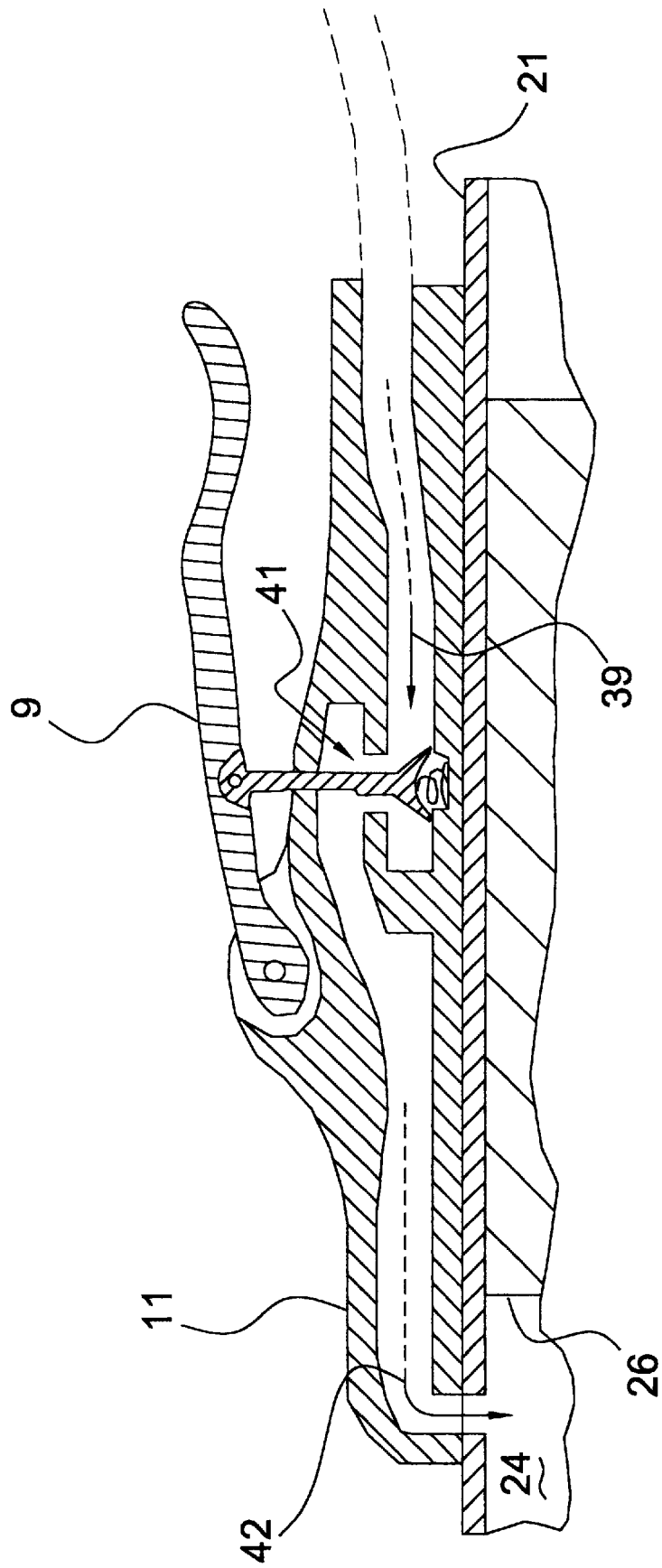
FIG. 3 is a cross-sectional schematic of a pneumatic valve suitable for finger actuated pulse modulation.

FIG. 3 illustrates by schematic cross section an simple embodiment of gas valve 11 suitable to allow highly selective gas flow modulation by user finger actuation of lever 9.

Pressurized gas 39 can be pulse width and pulse frequency modulated by valve 41 so that gas 42 flowing into cavity 24 of the medical actuator provides acceleration forces to free piston 26 appropriated to create the desired pulses of force.

As described with reference to FIGS. 1 and 2, piston 26 retracts from contact with stop 32 upon release of lever 9 and a bleed down of the gas pressure in cavity 24 by leakage and the gravitational weight of piston 26. Such retraction of the piston, whether only slightly or all the way to travel limiter 31 in FIG. 2, can also effectuated by moderated forces acting on the top of piston 26. Representative sources of such force include low pressure gas, springs, and other resilient materials. The inclusion of such refinements allows the use of the medical actuator in horizontal or even inverted orientations when the need arises.

Bleeding of the gas pressure from cavity 24 between successive actuations of valve 11 by the user, as an aspect of allowing piston 26 to move toward limiter 31 by action of gravity, will require an exhaust port if the various gas joints defining cavity 24 are efficiently sealed. For example, the addition of outer rings to free piston 26 could materially decrease the bleed gas passage thereabouts.

FIG. 2 shows travel limiter 31 as a relatively short cylindrical insert situated within the end of body 26 as fixes in position by threaded cap 22. Since the function is to limit the downward translation of free piston 26, it may be physically manifest by any element that so limits the travel of the piston. What is worth noting as to travel limiter 31 is that the relative size inherently limits the distance over which piston 26 may accelerated responsive to pressurized gas. As such, rest 31 establishes a maximum velocity and momentum for a piston of set mass and a set gas pressure. In applications where the magnitudes of the force pulses must be limited for the protection of the patient, selection of the travel limiter size provides a decree of safety.

Gas valve 11 is operationally described as the direct mechanism by which gas pressure is modulated. Other embodiments exist for providing modulated pulses of gas suitable to incrementally and successively accelerate free piston 26. For example, actuation by the user could involve the full enablement of an electronically or pneumatically modulated gas, or a valve modulating such gas characteristics, as alternative to direct finger control of the valve. This gas modulation control refinement is likely to be implemented where user dexterity or fatigue are considerations.

As noted hereinbefore, the medical actuator finds applications not only in orthopedic but also in orthodontic procedures. In an orthodontic application, the translation device would transfer pulling pulses to a tooth by virtue of a clasping of, or bonded attachment to, the tooth. All the features of the invention exist with equal import in such orthodontic application, from single handed operation to the selective control of the force pulses.

The medical actuator embodied in FIG. 2 provides an accentuated level of user control in part because it efficiently limits the kinds of transient forces imparted to the user's hand. The pulses of force provided by medical actuator 2 are a result of the interaction between moving free piston 26 and stop 32 of rod 12. Both free piston 26 and rod 12 are freely moveable independent of actuator body 21. Therefore, the vibrations created by the contact between free piston 26 and stop 32 are not conveyed directly to the user's hand. Only secondary vibrations are transferred to body 21. The pulses of force on shaft 12 are transmitted substantially intact to the medical translation device attached to the patient. The key forces that are conveyed to body 26, and thereby the user's hand, are associated with accelerating the piston from a travel limiiter defined rest location or an intermediate dynamic position. Even if the gas pressure could be applied instantaneously, which it is not, the forces experienced by the hand are minimal because the mass of the piston is relatively less than the combined mass of the actuator body, the caps, the gas valve parts, and the user's hand and arm. Air flow through holes 37 also provides limited compensation. The net effect is a medical actuator providing relatively steady single handed operation.

Though the invention has been described and illustrated by way of specific embodiments, the apparatus and methods encompassed by the invention should be interpreted in keeping with the breadth of the claims set forth hereinafter.

I claim:

1. A medical actuator, comprising:
   a tubular body having a first and a second end;
   a free piston slidable within the tubular body;
   a cap means for closing the first end of the tubular body;
   a shaft extending through the cap means and the free piston;
   means attached to the shaft for limiting movement of the piston toward the second end of the tubular body;
   means for positioning the piston proximate the first end of the tubular body;
   user controllable means for generating a selective pressure in a region between the piston and the cap means; and
   means for transferring movement in the shaft to an outside body, the movement of the shaft being responsive to contact between the piston and the means for limiting movement.

2. The apparatus recited in claim 1, wherein the means for transferring is an orthodontic or orthopedic translation device attachable to impute a force to a tooth or bone structure.

3. The apparatus recited in claim 2, wherein the user controllable means is a pulse modulated hand controllable pneumatic valve.

4. The apparatus recited in claim 3, wherein the pneumatic valve is capable of both pulse width and pulse frequency modulation.

5. The apparatus recited in claim 4, wherein the pneumatic valve is affixed to the tubular body to enable a human hand to hold the medical actuator while selectively enabling the pneumatic valve.

6. The apparatus recited in claim 1, wherein the user controllable means is a pulse modulated hand controllable pneumatic valve.

7. The apparatus recited in claim 6, wherein the pneumatic valve is capable of both pulse width and pulse frequency modulation.

8. The apparatus recited in claim 7, wherein the pneumatic valve is affixed to the tubular body to enable a human hand to hold the medical actuator while selectively enabling the pneumatic valve.

9. The apparatus recited in claim 1, wherein the shatt extends through the relative center of the piston.

10. A method for applying selectively modulated pulses of force using a hand operable medical actuator, comprising the steps of:
    mechanically attaching a shaft extending from the medical actuator to an orthopedic translation device attachable to impute a force to a tooth or bone structure;

introducing pneumatic gas into the medical actuator between a free piston slidable within the medical actuator and a closed end of the medical actuator;

modulating the pressure of the pneumatic gas to cause movement of the free piston within the medical actuator sufficient to impart modulated pulses of force through contact with a stop attached to the shaft; and transferring force pulses imparted by the free piston to the stop attached to the shaft through the mechanical attachment to the orthopedic translation device.

11. The method recited in claim 10, wherein the modulating step is accomplished using a hand controllable pneumatic valve.

12. The method recited in claim 11, wherein the step of modulating comprises both pulse width and pulse frequency modulation.

13. The method recited in claim 12, wherein the modulating is performed by the same hand which holds the medical actuator.

14. The method recited in claim 13, wherein the introducing step is accomplished by moving the piston in a direction away from the closed end of the medical actuator.

15. The method recited in claim 10, wherein the step of modulating comprises both pulse width and pulse frequency modulation.

16. The method recited in claim 15, wherein the modulating is performed by the same hand which holds the medical actuator.

17. The method recited in claim 16, wherein the introducing is accomplished by moving the piston in a direction away from the closed end of the medical actuator.

18. A medical actuator suitable to impart pulses of force through a translation device attached to tooth or bone structure, comprising:

a user positioned medical actuator body;

a free piston means movable within the medical actuator body;

a shaft extending through the free piston means and out through an opening in an end of the medical actuator body, the shaft being freely translatable over a material range of the shaft through the opening in the end of the medical actuator body;

means for moving the free piston means within the medical actuator body responsive to an introduction of pressurized gas;

means for a user of the medical actuator to selectively modulate the pressurized gas introduced into the medical actuator;

means for connecting a translation device to the shaft extending from the medical actuator body; and piston stop means connected to the shaft for generating pulse movement in the shaft with relative isolation from the medical actuator body responsive to contact with the free piston within the freely translatable range of the shaft.

19. The apparatus recited in claim 18, wherein the means for a user to selectively modulate is a pneumatic valve capable of both pulse width and pulse frequency modulation.

20. The apparatus recited in claim 18, wherein the means for a user to selectively modulate is a pneumatic valve affixed to the medical actuator to enable a human hand to hold the medical actuator while selectively enabling the pneumatic valve.

* * * * *